United States Patent [19]

Takai et al.

[11] Patent Number: 4,846,838

[45] Date of Patent: Jul. 11, 1989

[54] PROSTHETIC BODY FOR BONE SUBSTITUTE AND A METHOD FOR THE PREPARATION THEREOF

[75] Inventors: Nobuharu Takai; Hiroyasu Noma; Shoichi Wakabayashi; Susumu Takata, all of Tokyo, Japan

[73] Assignee: TDK Corporation, Tokyo, Japan

[21] Appl. No.: 65,083

[22] Filed: Jun. 18, 1987

Related U.S. Application Data

[60] Continuation of Ser. No. 810,652, Dec. 18, 1985, abandoned, which is a division of Ser. No. 628,474, Jul. 6, 1984, abandoned.

[30] Foreign Application Priority Data

Jul. 15, 1983 [JP] Japan ................................ 58-129087

[51] Int. Cl.$^4$ .......................... A61F 2/28; C04B 38/06
[52] U.S. Cl. ........................................ 623/16; 623/66; 501/83; 501/81; 501/82
[58] Field of Search ...................... 623/16, 66; 264/44, 264/59, 65; 128/92 R, 92 Q, 92, 96; 501/1, 81–84

[56] References Cited

U.S. PATENT DOCUMENTS

| | | | |
|---|---|---|---|
| 3,345,160 | 10/1967 | Miccioli et al. | 264/44 |
| 4,073,999 | 2/1978 | Bryan et al. | 623/66 X |
| 4,180,411 | 12/1979 | Whitman et al. | 501/83 |
| 4,195,366 | 4/1980 | Jarcho et al. | 501/84 X |
| 4,371,484 | 2/1983 | Inakai et al. | 264/44 |
| 4,467,043 | 8/1984 | Kriegesmann et al. | 264/65 |

FOREIGN PATENT DOCUMENTS 2485504 12/1981 France ................................ 623/16

Primary Examiner—Richard J. Apley
Assistant Examiner—Alan W. Cannon
Attorney, Agent, or Firm—Wyatt, Gerber, Burke and Badie

[57] ABSTRACT

The inventive prosthetic body for bone substitute is a sintered body of hydroxyapatite and characterized by the open pore structure with a pore diameter in a specified range forming a porosity of 20 to 40% and a bending strength of at least 100 kg/cm$^2$. The sintered body can be prepared by blending powders of hydroxyapatite and a thermally decomposable substance, e.g. crystalline cellulose, each having a specified particle size distribution, in a specified proportion and shaping and sintering the powder blend.

9 Claims, No Drawings

PROSTHETIC BODY FOR BONE SUBSTITUTE AND A METHOD FOR THE PREPARATION THEREOF

This is a continuation of Ser. No. 810,652, filed Dec. 18, 1985, now abandoned, which is a division of application Ser. No. 628,474, filed on July 6, 1984, and now abandoned.

BACKGROUND OF THE INVENTION

The present invention relates to a novel prosthetic body for bone substitute formed of a sintered porous hydroxyapatite and a method for the preparation thereof.

Along with the progress of the medical engineering in recent years, intensive investigations are now under way for an artificial material of a bone substitute used in the prosthesis of the bones lost by a traffic accident or some diseases such as bone tumors. Such a prosthetic body for bone substitute to be embedded in the human body should of course satisfy various rather difficult requirements that the material has no toxicity to living body to be usable with safety and the mechanical strength thereof should be sufficiently large to approximate the strength of natural bones. In addition, it is desirable that the prosthetic body embedded in the living body can spontaneously disappear to be replaced with the neogenetic bones.

A great variety of artificial materials have been proposed as a prosthetic body for bone substitute although none of them is quite satisfactory in one or more respects, among which hydroxyapatite is one of the most promising prosthetic materials. Hydroxyapatite is a mineral expressed by the chemical formula $Ca_{10}(PO_4)_6(OH)_2$ which is the principal constitutent of bones and teeth of vertebrate animals so that the sintered body prepared thereof is promising as a prosthetic body for bone and tooth substitutes by virtue of the affinity thereof to the tissues of human body. Indeed, many investigations have been dedicated to the development of this material for the practical applications thereof as a prosthetic body.

The hitherto developed prosthetic bodies of hydroxyapatite are, however, also not without problems. In order that a prosthetic body embedded in the living body is rapidly and firmly bonded to the tissue of the living body, for example, it is a desirable condition that at least the surface layer of the prosthetic body has a certain degree of porosity so that the living body tissue can enter the pores to anchor the prosthetic body at the position. Such a requirement for porosity of a sintered prosthetic body is incompatible with the requirement for a mechanical strength of the body as large as possible and the mechanical strength of a sufficiently porous sintered body cannot be large enough to ensure its application as a bone substitute. Thus, no prosthetic body with practical applicability has yet been obtained by sintering hydroxyapatite.

SUMMARY OF THE INVENTION

It is therefore an object of the present invention to provide a novel and improved prosthetic body for bone substitute formed of sintered hydroxyapatite having a porosity to ensure anchoring of the living body tissue when the prosthetic body is embedded in the living body along with a mechanical strength large enough to ensure the applicability thereof as a bone substitute.

Another object of the invention is to provide a reliable and convenient method for the preparation of such a prosthetic body formed of sintered hydroxyapatite.

Thus, the prosthetic body for bone substitute provided by the present invention is a sintered body of hydroxyapatite having a porosity in the range from 20 to 40% formed of open pores with a pore diameter in the range from 10 to 100 μm and having a bending strength of at least 100 kg/cm².

The method of the invention for the preparation of the prosthetic body for bone substitute formed of a sintered body of hydroxyapatite and defined by the specific porosity and pore diameter of the open pores and the high value of the bending strength as mentioned above consisting essentially of the steps of: blending 100 parts by weight of a powder of hydroxyapatite having an average particle diameter in the range from 0.1 to 10 μm with from 10 to 40 parts by weight of a thermally decomposable substance having an average particle diameter in the range from 10 to 100 μm to give a powder blend; shaping the powder blend into a desired form; and sintering the thus shaped form of the powder blend at a temperature in the range from 900° to 1400° C.

It is preferable that the sintering of the shaped form of the powder blend above mentioned is performed by use of a hot press under a pressure of 300 to 1000 kg/cm² at a temperature of 900° to 1400° C.

DETAILED DESCRIPTION OF THE PREFERRED EMBODIMENTS

The above described novel prosthetic body and the method for the preparation thereof have been developed as a result of the extensive investigations continued by the inventors to develop an artificial material usable as a prosthetic bone substitute having excellent mechanical strengths and capable of being rapidly dissolved and absorbed in a living body to be replaced with the neogenetic bones leading to the discovery that a sintered body of hydroxyapatite may have a porous structure of open pores and is suitable for the purpose only when the sintered body has been prepared under very specific limited conditions.

The base starting material used in the inventive method is a powder of hydroxyapatite of which the origin or the method of preparation is not particularly limitative including the synthetic hydroxyapatites prepared in a known method of wet or dry process and the living-body hydroxyapatite extracted from the bones and teeth of vertebrate animals. The particle size distribution of the powdery hydroxyapatite should be as fine as possible from the standpoint of the favorable sintering behavior thereof though under practical limitations by the performance of the pulverizing machine and particle-size classifier as well as a problem involved in the handling of an excessively fine powder. The powder of the hydroxyapatite should usually have an average particle diameter in the range from 0.1 to 10 μm.

The thermally decomposable substance blended with the powder of hydroxyapatite is a particulate or fibrous polymeric material capable of being decomposed into gaseous decomposition products without leaving any solid residue, e.g. carbon, when a shaped body of the powder blend of hydroxyapatite therewith is heated at the specified temperature, to form open pores behind surrounded by the skeleton of the sintered hydroxyapatite. Accordingly, it should have an average particle diameter in the range from 10 to 100 μm with preference of a particulate material to fibrous materials in view of the easiness of blending with hydroxyapatite. The thermally decomposable substance here defined should preferably be insoluble in a solvent, e.g. water, when powders are blended by wet blending using a solvent or with admixture of a solution of a binder mentioned below. Examples of suitable thermally decomposable substance include crystalline cellulose powder, fibrous cellulose, polyurethanes, polyethylenes, nylon resins, acrylic resins and the like.

The amount of the thermally decomposable substance in the powder blend should preferably be in the range from 10 to 40 parts by weight per 100 parts by weight of the powder of hydroxyapatite. Deficiency in the amount of the thermally decomposable substance may result in the insufficiently developed open pore structure while an excessively large amount thereof unavoidably leads to the decrease in the apparent density and hence mechanical strength of the sintered body.

Blending of the powder of the thermally decomposable substance with the powder of hydroxyapatite can be performed in any known method provided that uniformity of the powder blend can be ensured thereby. For example, powders of the hydroxyapatite and the thermally decomposable substance can be directly blended together as such by use of a suitable blending machine for powders. Alternatively, the powder of hydroxyapatite is first granulated into granules having a particle diameter in the range, for example, from 20 to 200 $\mu$m which are then blended with the powder of the thermally decomposable substance. Further alternatively, the powder of the thermally decomposable substance is moistened with a suitable liquid, e.g. water, and the thus moistened powder of the thermally decomposable substance is then uniformly dusted with the powder of the hydroxyapatite.

The powder blend prepared in this manner is then admixed, if necessary, with a binder, which is preferably a water-soluble polymer such as a polyvinyl alcohol, in the form of a solution and the powder blend is shaped into a desired form which is subjected to sintering at a temperature in the range from 900° to 1400° C. The length of time for the sintering is usually in the range from 0.5 to 3 hours. Use of a hot press is preferable when further improvement in the mechanical strength is desired. The pressure in the hot press should be in the range from 300 to 1000 kg/cm$^2$ from the practical standpoint although any smaller pressure may have an advantageous effect in its own way. A pressure larger than 1000 kg/cm$^2$ has no further advantages.

The sintered body of hydroxyapatite obtained in the above described procedure has open pores with a diameter in the range from 10 to 100 $\mu$m, a porosity in the range from 20 to 40% and a bending strength of at least 100 kg/cm$^2$ and suitable for use as a prosthetic body for bone substitute.

The prosthetic body for bone substitute of the invention is, when it is embedded in a living body, susceptible to the attack of the osteoclasts having a dimension of 50 to 100 $\mu$m and rapidly dissolved and absorbed to be replaced with the neogenetic bone by the osteoblasts so that the prosthetic body of the invention is satisfactorily used in the therapeutic treatment in the stomatoplasty and orthopedics.

In the following, the present invention is described in more detail by way of examples.

EXAMPLE 1

Hydroxyapatite synthesized in a wet process was calcined at 900° C. for 1 hour and then pulverized in a ballmill into a fine powder having an average particle diameter of about 0.5 $\mu$m. The thus pulverized hydroxyapatite was admixed with 2% by weight of a polyvinyl alcohol in the form of an aqueous solution as a binder and the mixture was granulated into granules having a particle diameter of 50 to 100 $\mu$m.

A 100 parts by weight portion of the thus obtained granules was uniformly blended with 30 parts by weight of a crystalline cellulose having a particle size distribution in the range from 20 to 120 $\mu$m with an average particle diameter of about 100 $\mu$m, about 90% by weight of the particles having a diameter of 80 to 120 $\mu$m. The blend of the granules and the powder of crystalline cellulose was shaped into a form by compression molding under a molding pressure of 500 kg/cm$^2$ followed by sintering at 1350° C. for 1 hour.

The thus prepared sintered body had a porosity of about 26% formed of open pores of a diameter in the range from 20 to 100 $\mu$m and a bending strength of 127.4 kg/cm$^2$. The pore diameter was determined on the microphotograph of a cross section of the sintered body taken by use of a scanning electron microscope.

EXAMPLE 2

A 100 parts by weight portion of the same calcined and pulverized hydroxyapatite as used in Example 1 was uniformly blended with 30 parts by weight of the same crystalline cellulose with admixture of 2 parts by weight of a polyvinyl alcohol in the form of an aqueous solution and the powder blend was shaped into a form by compression molding under a molding pressure of 500 kg/cm$^2$ followed by sintering at 1350° C. for 1 hour.

The thus prepared sintered body of hydroxyapatite had substantially the same physical properties as that prepared in Example 1.

EXAMPLE 3

Small pieces of porous hydroxyapatite each having dimensions of 3 mm by 4 mm by 6 mm were prepared by cutting the sintered body prepared in Example 2 and, after sterilization in a conventional manner, five of them were embedded each in the mandible of a rabbit having a body weight of 2.5 to 3.0 kg. After three months of raising, the rabbits were killed and the condition of the embedded piece was dissectively examined to find that the sintered body of hydroxyapatite had been partly absorbed and the surface of the sintered body was firmly bonded to the neogenetic bone with good anchoring in each of the five rabbits.

Thus, it is a conclusion from the results of the above described animal test that the sintered hydroxyapatite body of the invention is quite satisfactorily usable in the clinical prosthesis at least as a bone substitute for lost maxillae.

EXAMPLE 4

Substantially the same experimental procedure as in Example 2 was repeated excepting the replacement of the crystalline cellulose powder with the same amount of a polyethylene powder having an average particle diameter of about 100 $\mu$m. The thus obtained sintered body of hydroxyapatite had approximately the same properties as that prepared in Example 2.

EXAMPLE 5

Substantially the same experimental procedure as in Example 2 was repeated except that the sintering was performed in a hot press at 1350° C. for 1 hour under a pressure of 500 kg/cm². The thus prepared sintered body had a porosity of 28% formed of open pores of 20 to 100 μm pore diameter and a bending strength of 186.5 kg/cm².

What is claimed is:

1. A method for the preparation of a prosthetic body for bone substitute, which consists essentially of a sintered body of hydroxyapatite having a porosity in the range from 20 to 40% formed of open pores with a pore diameter in the range from 10 to 100 μm and having a bending strength of at least 100 Kg/cm² which consists essentially of:
   1: blending with or without a binder 100 parts by weight of a powder of hydroxyapatite having an average particle diameter in the range from 0.1 to 10 μm with from 10 to 40 parts by weight of a thermally decomposable substance having an average particle diameter in the range of from 10 to 100 μm to give a powder blend;
   2: shaping the powder blend into a selected form; and
   3: sintering the shaped form of powder blend at a temperature in the range from 900° to 1400° C.

2. A method as in claim 1 wherein the thermally decomposable substance is crystalline cellulose powder or fibrous cellulose.

3. A method as in claim 1 employing a binder which is a water soluble polymer.

4. A method as in claim 3 wherein the binder is polyvinyl alcohol.

5. A method as in claim 2 employing a binder which is a water soluble polymer.

6. A method as in claim 5 wherein the binder is polyvinyl alcohol.

7. A method as in claim 1 wherein the thermally decomposable substance is polyurethane, polyethylene, nylon resin or acrylic resin.

8. A method as in claim 7 including the additional step of mixing the powder blend with an aqueous solution containing a binder which is a water soluble polymer.

9. A method as in claim 8 wherein the binder is polyvinyl alcohol.

* * * * *